(12) United States Patent
Takeuchi et al.

(10) Patent No.: US 12,004,507 B2
(45) Date of Patent: Jun. 11, 2024

(54) DEVICE FOR TRANSPORTING GRAFT

(71) Applicant: TERUMO KABUSHIKI KAISHA, Tokyo (JP)

(72) Inventors: Ryohei Takeuchi, Kanagawa (JP);
Tetsuya Yamaguchi, Kanagawa (JP);
Toshikazu Takeuchi, Kanagawa (JP);
Yosuke Kuruma, Kanagawa (JP);
Kenta Mizumoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 743 days.

(21) Appl. No.: 17/144,434

(22) Filed: Jan. 8, 2021

(65) Prior Publication Data

US 2021/0127664 A1 May 6, 2021

Related U.S. Application Data

(63) Continuation of application No. PCT/JP2019/027124, filed on Jul. 9, 2019.

(30) Foreign Application Priority Data

Jul. 10, 2018 (JP) .................................. 2018-130560
Dec. 18, 2018 (JP) .................................. 2018-236019

(51) Int. Cl.
*A01N 1/02* (2006.01)
*B25J 15/00* (2006.01)
(52) U.S. Cl.
CPC ........... *A01N 1/0273* (2013.01); *A01N 1/021* (2013.01); *B25J 15/0033* (2013.01)

(58) Field of Classification Search
None
See application file for complete search history.

(56) References Cited

U.S. PATENT DOCUMENTS 8,703,074 B2 4/2014 Nozaki
11,312,933 B2 4/2022 Katou et al.
(Continued)

FOREIGN PATENT DOCUMENTS

CN 102556510 A 7/2012
CN 204661737 U 9/2015
(Continued)

OTHER PUBLICATIONS

Office Action (The First Office Action) dated Mar. 23, 2023, by the National Intellectual Property Administration, P. R. China in corresponding Chinese Patent Application No. 201980043082.9, with Search Report. (8 pages).

(Continued)

*Primary Examiner* — P. Kathryn Wright
(74) *Attorney, Agent, or Firm* — BUCHANAN INGERSOLL & ROONEY PC

(57) ABSTRACT

A device for transporting objects such as a graft is configured to efficiently establish a liquid-tight state with a simple operation. The device is to be used in a state of being detachably attached to a container for storing a graft, the device including: a lid member for sealing the container; and an annular member for forming a first space by being interposed between the lid member and the container, wherein a second space is formed between the lid member and an inside surface of the container.

17 Claims, 3 Drawing Sheets

(56) References Cited

U.S. PATENT DOCUMENTS

| | | | |
|---|---|---|---|
| 2007/0166819 A1* | 7/2007 | Ghosh | C12M 23/10 |
| | | | 435/305.4 |
| 2012/0160714 A1* | 6/2012 | Nozaki | C12M 21/08 |
| | | | 206/205 |
| 2014/0302602 A1 | 10/2014 | Kawasaki | |
| 2015/0231628 A1 | 8/2015 | Nozaki et al. | |
| 2018/0177181 A1* | 6/2018 | Katou | A61J 1/1406 |
| 2019/0225926 A1* | 7/2019 | Katou | A01N 1/0273 |

FOREIGN PATENT DOCUMENTS

| | | | |
|---|---|---|---|
| CN | 106244415 A | | 12/2016 |
| JP | H0630760 A | | 2/1994 |
| JP | 2009089715 A | | 4/2009 |
| JP | 2012130311 A | | 7/2012 |
| JP | 2013128457 A | * | 7/2013 |
| JP | 2013128457 A | | 7/2013 |
| JP | 2013128458 A | | 7/2013 |
| JP | 2015043751 A | | 3/2015 |
| WO | WO-2005037986 A1 | * | 4/2005 ........... C12N 5/0698 |
| WO | 2013094370 A1 | | 6/2013 |
| WO | 2013/176106 A1 | | 11/2013 |
| WO | 2014041593 A1 | | 3/2014 |
| WO | 2016208018 A1 | | 12/2016 |
| WO | WO-2016208018 A1 | * | 12/2016 ........... A01N 1/0242 |
| WO | 2018003073 A1 | | 1/2018 |
| WO | 2019017464 A1 | | 1/2019 |
| WO | 2019124339 A1 | | 6/2019 |

OTHER PUBLICATIONS

English translation of the Office Action (Notice of Reasons for Refusal) dated Apr. 25, 2023, by the Japan Patent Office in corresponding Japanese Patent Application No. 2020-530193. (6 pages).

Office Action (Notice of Reasons for Refusal) dated Sep. 27, 2023, by the Japan Patent Office in corresponding Japanese Patent Application No. 2020-530193 and an English translation of the Office Action. (7 pages).

International Search Report (with English Translation) and Written Opinion issued in corresponding International Patent Application No. PCT/JP2019/027124, 11 pages (dated Sep. 24, 2019).

* cited by examiner

FIG. 1
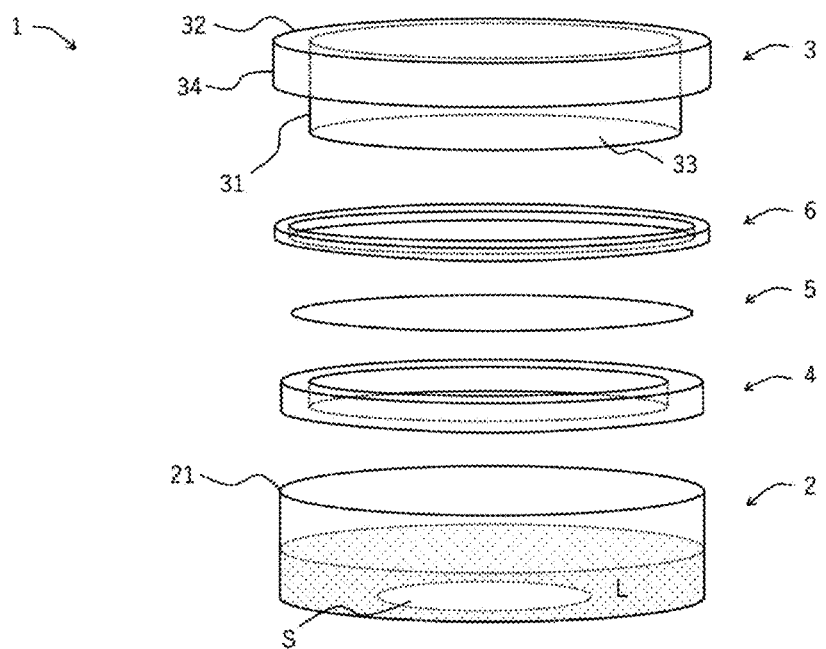
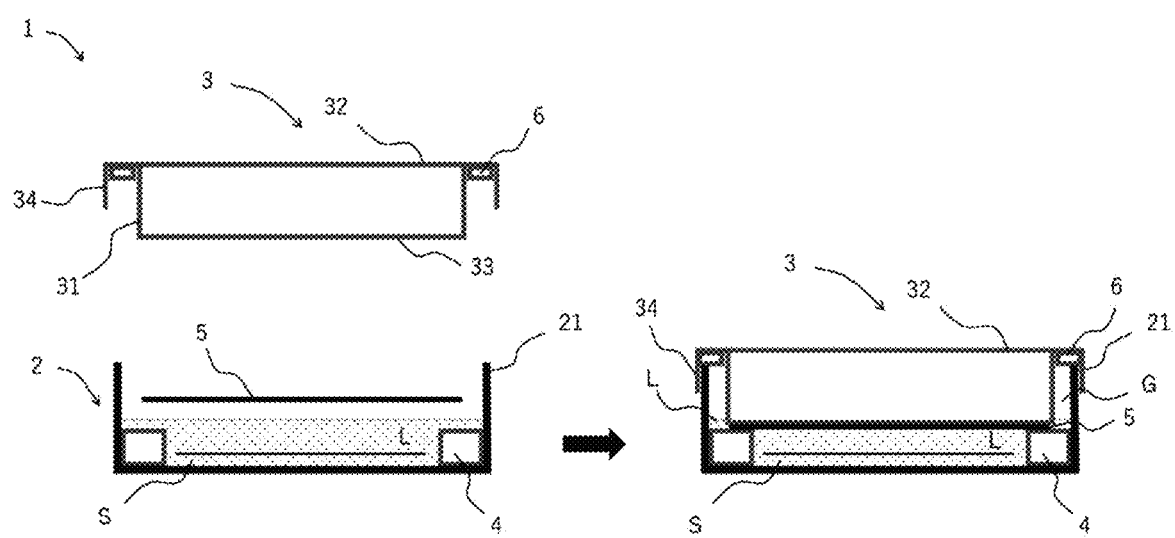
FIG. 2(A)   FIG. 2(B)

DEVICE FOR TRANSPORTING GRAFT

CROSS-REFERENCES TO RELATED APPLICATIONS

This application is a continuation of International Application No. PCT/JP2019/027124 filed on Jul. 9, 2019, which claims priority to Japanese Patent Application No. 2018-130560 filed on Jul. 10, 2018 and Japanese Patent Application No. 2018-236019 filed on Dec. 18, 2018, the entire content of which is incorporated herein by reference.

FIELD OF THE INVENTION

The present invention generally relates to a device for transporting a graft and a gripping tool for gripping or holding a graft-transporting device.

BACKGROUND DISCUSSION

In recent years, new regenerative medicine has been developed as a solution to the treatment of severe cardiac failure. As an example, a method of applying a sheet-shaped cell culture prepared using a temperature-responsive culture dish devised by tissue engineering to the surface of a heart has been attempted to treat severe cardiac infarction, or the like. The method using a sheet-shaped cell culture is capable of safely transplanting a large amount of cells over a wide range, and is particularly effective for, for example, cardiac infarction (including chronic cardiac failure associated with cardiac infarction), dilated cardiomyopathy, ischemic cardiomyopathy, and cardiac diseases (e.g., cardiac failure, particularly, chronic cardiac failure) associated with systolic dysfunction (e.g., left ventricular systolic dysfunction).

In order to clinically apply such a sheet-shaped cell culture, it is necessary to, for example, store the prepared sheet-shaped cell culture in a container together with a preservation solution and transport the container to an intensive care unit where transplantation is performed. However, the sheet-shaped cell culture inherently has a low physical strength, and thus, is susceptible to wrinkles, tears, damage, etc. that occur due to vibration during the transportation of the container. Therefore, transporting the container requires advanced technique and great care.

In order to meet such needs, various methods and containers have been developed. For example, in a container for storing and transporting a membranous tissue disclosed in Japanese Patent Application Publication No. 2012-130311, a storage section is filled with a preservation solution to an extent that a gas layer is not formed in the storage section, whereby sloshing or movement of the preservation solution can be prevented. Thus, vibration is not transmitted to the membranous tissue, so that damage of the membranous tissue can be prevented.

Japanese Patent Application Publication No. 2009-89715 discloses a package for transporting a cultured cell sheet. When the package is sealed with a lid, air is discharged together with a little amount of liquid culture medium. Therefore, even if the cultured cell sheet package shakes during transportation, air bubbles do not move in the liquid culture medium, which can prevent displacement and defect of the cultured cell sheet.

SUMMARY

As mentioned above, containers for safely transporting a fragile cell sheet have been developed. Further, such containers are designed to be liquid-tight so that air bubbles do not move in the container.

However, a high level of technique is required to completely remove air bubbles from the inside of the container and achieve a liquid-tight state. Moreover, since a strong force is required to remove the lid from the liquid-tight container, the liquid may be wavy when the lid is attached and detached, which may damage the cell sheet.

Disclosed here is a device capable of efficiently achieving a liquid-tight state by a simple operation.

[1] According to one aspect, a device is to be detachably attached to a container that possesses an inside surface upstanding from a bottom surface and an open end opposite the bottom surface, and that contains a graft. The device comprises: an annular member that surrounds a first space, with the annular member being positionable in the container so that the graft is located in the first space; and a lid positionable at the open end of the container to seal the container, with the lid being positionable at the open end of the container after the annular member is positioned in the container so that the annular member is interposed between the lid and the bottom surface of the container. The lid is configured so that when the lid is positioned at the open end of the container to seal the container, a second space exists between the lid and the inside surface of the container.

[2] The device according to [1], further including a sealing member interposed between the container and the lid member.

[3] The device according to [1] or [2], further including a protective member interposed between the annular member and the lid member to protect the first space.

[4] The device according to [3], wherein the protective member is flexible.

[5] The device according to [1] or [3], wherein the protective member and/or the lid member is water repellent.

[6] The device according to any one of [1] to [5], wherein the graft is a sheet-shaped cell culture.

[7] The device according to [6], wherein the sheet-shaped cell culture is a laminate.

[8] Another aspect involves a gripping tool including: a cover member; and a base member, the gripping tool being configured to press and grip the device according to any one of [1] to [7] from above and below.

The device can efficiently achieve a liquid-tight state with a simple mechanism and a simple operation, thereby providing great advantages in terms of operability and manufacturing cost. Further, the device can bring the inside of the container into a complete liquid-tight state. Therefore, entry of air bubbles (gas) into the container can be prevented, and thus, a fragile object is not damaged due to the movement of air bubbles within the container caused by, for example, shaking of the container during transportation. Particularly when the fragile object is a laminate of sheet-shaped cell cultures, displacement or defect of the laminate due to the movement of air bubbles can be prevented. Therefore, the fragile object can be stored for a long time with the shape of the fragile object in the liquid being retained without being deformed.

The device allows the liquid-tight state to be easily released. Therefore, vibration of the container and the movement of the liquid caused by, for example, forced removal of the lid member by a worker can be minimized, and thus, damage of the fragile object can be prevented. In addition, since the device allows the worker to do the work without contaminating the surroundings, the device is suitable for use in a location where cleanliness is strictly controlled, such as a bio-clean room used for preparing a sheet-shaped cell culture and an intensive care unit where a sheet-shaped cell culture is used.

According to another aspect, a graft-transporting device for transporting a graft comprises: a container having an interior in which is positioned liquid and a graft, with the container including a bottom surface and a side wall extending upwardly away from the bottom surface, and the side wall possessing an inner surface so that the bottom surface and the inner surface of the side wall surround the interior of the container. The container also includes an open end. An annular member surrounds a centrally located first space and is positioned in the container so that the graft is located in the centrally located first space. A lid is positioned at and closes the open end of the container to seal the interior of the container, and a second space exists in the interior of the container between the lid and the inner side wall surface of the container.

According to a further aspect, a method comprises: positioning an annular member in an interior of a container by introducing the annular member through an open end of the container, wherein the container includes a bottom surface positioned opposite the open end and an inside surface extending away for the bottom surface so that the interior of the container is surrounded by the bottom surface and the inside surface, with the annular member being configured so that the annular member surrounds a first space and the annular member being located in the container so that a graft and liquid are in the first space. The method also involves positioning a lid on the open end of the container to seal the container while the annular member is positioned in the interior of the container so that the annular member is interposed between the lid and the bottom surface of the container. The lid is positioned on the open end of the container so that a second space exists between the lid and the inside surface of the container.

BRIEF DESCRIPTION OF THE DRAWINGS

FIG. 1 is a conceptual diagram of a device 1 according to a first embodiment.

FIGS. 2(A) and 2(B) are cross-sectional views of the device 1 shown in FIG. 1.

DETAILED DESCRIPTION

Figure 3:
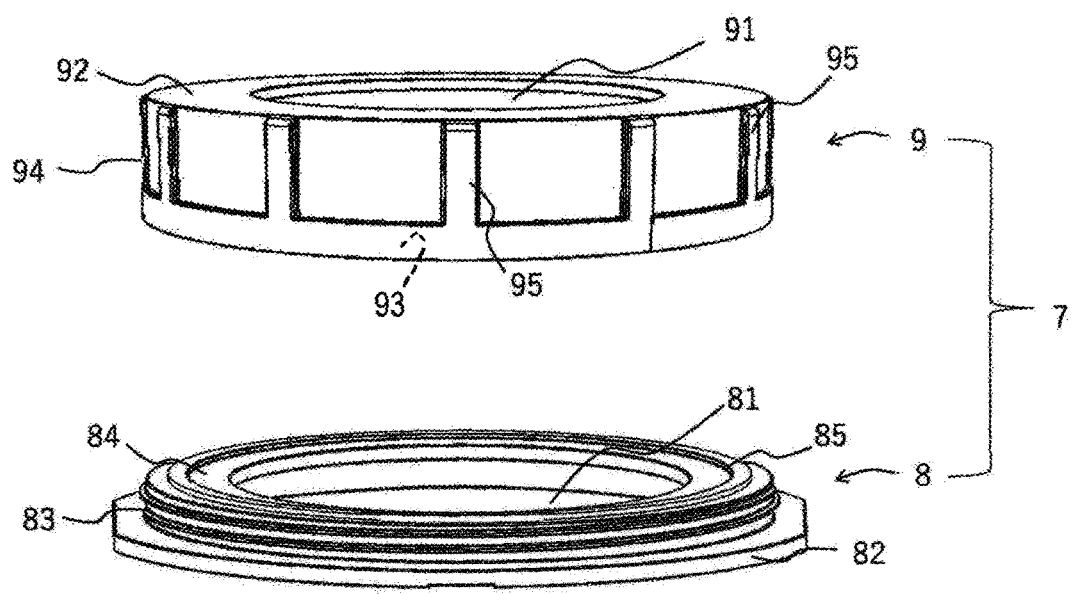
FIG. 3 is a perspective view of a gripping tool 7 according to a second embodiment.

The term "fragile object" as used here denotes any object which has such low physical strength as to tear, break, deform, or the like when a liquid moves. Examples of such objects include an object having a thin-walled part, a band-shaped object, and a sheet-shaped object. Examples of the sheet-shaped object include, but are not limited to, a sheet-shaped structural object, for example, a flat membranous tissue formed from a biologically derived material such as a sheet-shaped cell culture, and various kinds of films formed from plastic, paper, woven cloth, unwoven cloth, metal, polymer, lipid, etc. Among these, objects that hardly decompose or disintegrate in a liquid are preferable. The sheet-shaped structural object may have, for example, a polygonal shape or a circular shape, and may vary in width, thickness, diameter, etc. The sheet-shaped structural object in the present invention may be used in a monolayer form or as a laminate in which the two or more sheet-shaped structural objects are laminated. When the sheet-shaped structural objects are used as a laminate, layers of the object laminate may be joined together or separated from one another. If the layers are joined together, overlapped parts of the layers may be entirely or partially joined to one another. Further, as used here, the term "fragile" means that it is difficult or substantially impossible to evaluate tensile properties of an object due to its fragility with, for example, a conventional tensile tester (for example, a tester specified in JIS K 7161 etc.) in which the object is fixed to a gripping tool outside the liquid. Examples of such a fragile object include an object whose tensile properties are difficult to be accurately measured by a conventional tensile tester because values associated with the tensile properties are small. Examples of such fragile objects include those that exhibit a breaking load of less than 10 N (Newton), less than 5 N, less than 2 N, less than 1 N, less than 0.5 N, less than 0.1 N, and less than 0.05 N when subjected to a tensile test. Further, the measurement limit of the conventional tensile test regarding a breaking load is generally about 1 N, and therefore, in one aspect of the present invention, an object exhibiting a breaking load lower than 1 N (for example, less than 0.5 N) is preferable as a fragile object.

In the present invention, the term "graft" denotes a biologically derived fragile object having a relatively low physical strength. The graft includes cultured cells (for example, cell cultures, etc.) and harvested cells. The graft may further include products produced by cells. The graft may also include a material (filling material or supporting material) for filling and/or supporting a predetermined part of the living body (for example, a diseased part), in addition to cells and/or cell products. The graft may have various shapes such as a sheet shape, a membranous shape, a lump shape, and a column shape. The graft is used for transplantation into a living body. Examples of the graft include three-dimensional cell tissues (organoids, spheroids, etc.), and two-dimensional cell tissues (sheet-shaped cell cultures, etc.).

The term "sheet-shaped cell culture" as used here denotes a cell culture which resembles a sheet having cells joined together. The cells may be joined together directly (including the case where the cells are joined together with cellular elements such as adhesion molecules therebetween) and/or via an intervening substance therebetween. The intervening substance is not particularly limited so long as it is capable of joining cells together at least physically (mechanically). Examples thereof include an extracellular matrix. Preferably, the intervening substance is derived from cells, particularly derived from cells constituting the sheet-shaped cell culture. The cells can be joined together at least physically (mechanically) and may be further joined together functionally, for example chemically or electrically. The sheet-shaped cell culture may consist of one layer of cells (may have a monolayer form), or two or more layers of cells (may have a multilayer form). Further, the sheet-shaped cell culture may have a three-dimensional structure having a thickness exceeding the thickness of one cell without the cells exhibiting a clear layered structure. For example, in the vertical cross section of the sheet-shaped cell culture, the cells may be present in a state of being arranged nonuniformly (for example, in a mosaic) without being uniformly aligned in the horizontal direction. The sheet-shaped cell culture may be a single sheet-shaped cell culture which is independently formed, or may be a laminate formed by laminating two or more independent sheet-shaped cell cultures. The laminate may have two, three, four, five, or six layers of sheet-shaped cell cultures.

The sheet-shaped cell culture involved here includes any cells capable of forming the above-mentioned structure. Non-limiting examples of such cells include adherent cells. The adherent cells include, for example, adherent somatic cells and stem cells. Examples of the somatic cells include cardiac muscle cells, fibroblasts, epithelial cells, endothelial cells, hepatic cells, pancreatic cells, kidney cells, adrenal cells, periodontal ligament cells, gingival cells, periosteal cells, dermal cells, synovial cells, and cartilage cells. Examples of the stem cells include myoblasts, tissue stem cells such as cardiac stem cells, embryonic stem cells, pluripotent stem cells such as induced pluripotent stem (iPS) cells, and mesenchymal stem cells. The somatic cells may be those that are obtained by differentiation from stem cells, especially iPS cells. Non-limiting examples of the cells capable of forming the sheet-shaped cell culture include myoblasts (for example, skeletal myoblasts), mesenchymal stem cells (for example, those which are derived from bone marrow, fat tissues, peripheral blood, skin, hair root, muscle tissues, endometrium, placenta, and cord blood), cardiac muscle cells, fibroblasts, cardiac stem cells, embryonic stem cells, iPS cells, synovial cells, cartilage cells, epithelial cells (for example, oral mucosal epithelial cell, retinal pigment epithelial cells, and nasal mucosal epithelial cells), endothelial cells (for example, vascular endothelial cells), hepatic cells (for example, hepatic parenchymal cells), pancreatic cells (for example, islet cells), kidney cells, adrenal cells, periodontal ligament cells, gingival cells, periosteal cells, and dermal cells. In the present specification, cells which form mono-layered cell cultures, such as myoblast or cardiac muscle cells, are preferable, and most preferable cells are skeletal myoblasts or iPS cell-derived cardiac muscle cells.

The cells can be derived from any living organism that can be cured with the help of cell culture. Such living organisms are not particularly limited, and examples thereof include human, primate, dog, cat, pig, horse, goat, and sheep. The sheet-shaped cell culture may be prepared from one species of cells or more than one species of cells. According to a preferred embodiment, in a case where the cell culture is prepared from more than one species of cells, the major cells account for 65% or more, preferably 70% or more, and more preferably 75% or more of the total cells in the cell culture (in the case of using, for example, skeletal myoblasts), when the cell culture is prepared completely. The percentage represents purity.

The sheet-shaped cell culture in the present invention may be a cultured tissue in a sheet form which is obtained by inoculating cells onto a scaffold (support for cell culturing) and culturing the cells. However, it is preferable that the sheet-shaped cell culture is composed solely of substances derived from the cells constituting the cell culture, and does not contain other substances.

The sheet-shaped cell culture may be prepared by any known method.

In one aspect, the sheet-shaped cell culture is a sheet-shaped cell culture of skeletal myoblasts. The sheet-shaped cell culture of skeletal myoblasts may be vulnerable to breaking by its own weight even when a part of the sheet-shaped cell culture is pinched. Thus, the sheet-shaped cell culture cannot be transported in its isolated form. Moreover, it is extremely difficult to restore the sheet-shaped cell culture into its original form once it is folded. Consequently, keeping the sheet form in a liquid can be of great significance.

The container is not particularly limited so long as it is capable of holding inside a fragile object, a liquid, or the like and is capable of preventing the liquid from leaking form the container. Any container, including commercially available containers, may be used. Examples of the material of the container include, but are not limited to, polyethylene, polypropylene, Teflon (registered trademark), polyethylene terephthalate, polymethyl methacrylate, nylon 6,6, polyvinyl alcohol, cellulose, silicone, polystyrene, glass, polyacrylamide, polydimethylacrylamide, and metal (for example, iron, stainless steel, aluminum, copper, or brass). In addition, the container preferably has at least one flat bottom surface for keeping the shape of the fragile object. Examples of such container include, but are not limited to, a petri dish, a cell culture dish, and a cell culture bottle. The area of the flat bottom surface is not particularly limited, but is typically 9.1 to 78.5 $cm^2$, 1.13 to 78.5 $cm^2$, preferably 12.6 to 78.5 $cm^2$, and more preferably 9.1 to 60.8 $cm^2$.

The liquid in the container is composed of at least one component which is not particularly limited. Examples of the liquid include water, aqueous solution, non-aqueous solution, suspension, and emulsion.

Moreover, the "solution" or "liquid" used in the present specification may be a fluid having fluidity as a whole, and may contain any other non-liquid components including solids such as a scaffold and air bubbles.

The liquid in the container may be composed of any components that have little effect on the fragile object. In a case where the fragile object is a membrane composed of materials derived from a living organism, biocompatible components, that is, components that cause no or at least little undesirable effects such as inflammatory reaction, immune reaction, or toxic reaction on the living organism and cells are preferably used as the components constituting the liquid in the container from a viewpoint of biological stability and long-term storage stability. Examples of such components include water, saline, biological buffer (such as HBSS, PBS, EBSS, Hepes, and sodium bicarbonate), culture medium (such as DMEM, MEM, F12, DMEM/F12, DME, RPMI1640, MCDB, L15, SkBM, RITC80-7, and IMDM), sugar solution (such as sucrose solution and Ficoll-paque (registered trademark) PLUS), sea water, serum-containing solution, Renografin (registered trademark) solution, metrizamide solution, meglumine solution, glycerin, ethylene glycol, ammonia, benzene, toluene, acetone, ethyl alcohol, benzole, oil, mineral oil, animal oil, vegetable oil, olive oil, colloidal solution, liquid paraffin, turpentine oil, linseed oil, and castor oil.

In a case where the fragile object is a sheet-shaped cell culture, the liquid in the container is preferably composed of components that can ensure stable cell storage, contain minimal oxygen and nutrients required for cell existence, and have an osmotic pressure low enough not to break cells. Examples of the components to meet these requirements include, but are not limited to, saline, biological buffer (such as HBSS, PBS, EBSS, Hepes, and sodium bicarbonate), culture medium (such as DMEM, MEM, F12, DMEM/F12, DME, RPMI1640, MCDB, L15, SkBM, RITC80-7, and IMDM), and sugar solution (such as sucrose solution and Ficoll-paque PLUS (registered trademark)).

The amount of the liquid in the container is not particularly limited, as long as the fragile object can be retained with the lid member being attached to the container, and the liquid level present between the bottom part of the container and the top part of the lid member is high enough to prevent the fragile object from moving (shaking) in the liquid. That is, when a space is created between the liquid surface and the lid member, the liquid (liquid surface) moves, and the fragile object easily moves in the liquid. Therefore, it is preferable to adjust the liquid level so that there is no space between the liquid surface and the lid member. In one aspect, the sheet-shaped cell culture has a diameter of about 35 to 55 mm and an area of 6 $cm^2$ or more, or 10 $cm^2$ or more. The liquid level can be set to, for example, 1.0 mm to 20.0 mm regardless of the diameter of the sheet-shaped cell culture.

The lid member is not particularly limited as long as it can seal the container. Examples of the material of the lid member include, but are not limited to, polyethylene, polypropylene, Teflon (registered trademark), polyethylene terephthalate, polymethyl methacrylate, nylon 6,6, polyvinyl alcohol, cellulose, silicone, polystyrene, glass, polyacrylamide, polydimethylacrylamide, and metal (for example, iron, stainless steel, aluminum, copper, or brass).

The shapes of the lid member and the container are not particularly limited as long as the lid member and the container can be engaged with each other and a closed space can be formed by such engagement. For example, in a case where the container is a general-purpose petri dish, the lid member preferably has a circular shape. Further, the lid member and/or the container may be made of a light-transmissive material so that the state of the fragile object contained in the container and the presence or absence of air bubbles in the liquid can be confirmed.

The fragile object is held in the liquid in the container containing the liquid. Although the position of the fragile object in the liquid is not particularly limited, the fragile object is placed at a position where the lid member and the fragile object do not come into contact with each other (or may come into contact with each other) while the lid member is attached to the container to form a closed space. Preferably, the fragile object is placed on the bottom surface of the container, near the bottom surface, or the like in the liquid in the container.

The term "water-repellent treatment" means that a solid surface is treated so that the contact angle, which is the angle formed by a liquid surface and the solid surface, is 90° or more at the boundary line where the solid surface and the liquid contact. For example, on a water-repellent solid surface that has been subjected to Teflon (registered trademark) coating or the like, the contact angle is nearly 180°, and the droplets are almost spherical. Therefore, even if a liquid is present between the water-repellent solid surfaces, the solid surfaces do not stick to each other. Examples of the water-repellent treatment method include a coating method for coating the solid surface with a resin such as Teflon (registered trademark), silicone, a fluorine-based water repellent agent, wax, alumina soap, pyridinium salt, or gelatin. Further, the water-repellent treatment may be a method for forming irregularities on the solid surface without using a coating agent, such as forming irregularities on the solid surface with laser, like a super water-repellent treatment.

The term annular member indicates a member having a space inside a ring formed by rotating a rectangle around an axis parallel to one side of the rectangle. That is, as shown in FIG. 1, the annular member surrounds a centrally located space. The height of the annular member is not particularly limited, but is typically 1 to 20 mm, preferably 3 to 15 mm, more preferably 5 to 10 mm so that the liquid and the fragile object can be contained in such a space. The inner diameter of the annular member is not particularly limited, but is typically 1 to 15 cm, preferably 3 to 15 cm, more preferably 3 to 10 cm.

The term sealing member indicates a member that is interposed between the container and the lid member to enhance the hermeticity of the container, and examples thereof include a packing ring.

The annular member and/or the sealing member can be made of an elastic material in order to absorb manufacturing tolerances of the container and the lid member and improve the hermeticity of the container. Examples of the elastic material include, but are not limited to, natural rubber, elastomer, nitrile rubber, and silicone rubber.

One aspect of the disclosure here relates to a device to be used in a state of being detachably attached to a container for storing a graft, the device including: a lid member for sealing the container; and an annular member for forming a first space by being interposed between the lid member and the container, wherein a second space is formed between the lid member and an inside surface of the container.

Preferred embodiments will now be described in detail with reference to the drawings. Set forth below with reference to the accompanying drawings is a detailed description of embodiments of a device and method for transporting a graft representing examples of the inventive transporting device and method disclosed here.

A first embodiment will be described with reference to FIGS. 1 and 2.

FIG. 1 is a conceptual diagram of a device 1 according to the first embodiment, and FIGS. 2(A) and 2(B) are sectional views of the device 1 shown in FIG. 1. In the drawings of the present application, the dimensions of the various components are exaggerated, as appropriate, for facilitating the understanding of the description, and they may differ from the actual dimensions.

As shown in FIG. 1, the device 1 according to the first embodiment includes a lid member or lid 3 for sealing a container 2, an annular member 4, a protective member 5, and a sealing member or seal 6. The container 2 is a commercially available petri dish having an end part 21 that surrounds an opening, and constitutes a storage space that can store a liquid L, a fragile object S, or the like. That is, as shown in FIGS. 1 and 2, the container possesses a bottom surface and an inner side wall surface extending upwardly away from the bottom surface so that the bottom surface and the inner side wall surface together surround the container interior that holds liquid L and the fragile object S. The lid member 3 includes a top part 32, a protruding part 31 extending downward from the top part 32, and a cylindrical skirt wall or side wall 34 hanging or extending from the peripheral edge of the top part 32. The protruding part 31 possesses a bottomed cylindrical shape having a bottom surface 33, and protrudes toward the internal space of the container 2 with the lid member 3 attached to the container 2. The outer diameter of the protruding part 31 is smaller than the inner diameter of the container 2, so that a space G (second space) is formed between the protruding part (outside surface of the protruding part) 31 and the inside surface of the container 2 when the lid member 3 is attached to the container 2. The cylindrical skirt wall 34 has an inner diameter larger than the outer diameter of the container 2, and functions as a guide mechanism for guiding the position of the protruding part 31 to the center of the container 2 when the lid member 3 is attached to the container 2.

The annular member 4 is a member having a space (first space) inside a ring formed by rotating a rectangle around an axis parallel to one side of the rectangle. The annular member 4 has an outer diameter substantially the same as or slightly larger than the inner diameter of the container 2 so that the annular member 4 can be placed on the bottom surface of the container 2 without displacement. The inner diameter of the annular member 4 is smaller than the outer diameter of the protruding part 31 so that, when the protruding part 31 is placed on the annular member 4, the protruding part 31 can be placed on the upper surface of the annular member 4 without entering the space inside the annular member 4 (i.e., without entering the central space surrounded by the annular member 4). The annular member 4 has a rectangular cross section, and is configured so that there is no space into which air bubbles will enter when the annular member 4 is immersed in the liquid. The annular member 4 is made of an elastic material. Therefore, when held between the lid member 3 and the container 2, the annular member 4 absorbs manufacturing tolerances of the container 2 and/or the lid member 3 to improve adhesion.

The protective member 5 is a member that is placed on the annular member 4 to protect the space inside the annular member 4. The diameter of the protective member 5 is larger than the inner diameter of the annular member 4 so that, when the protective member 5 is placed on the annular member 4, the protective member 5 can be placed on the upper surface of the annular member 4 without entering the space inside the annular member 4 (i.e., without entering the central space surrounded by the annular member 4). The protective member 5 is made of a fluid impermeable material so that gas and liquid do not pass therethrough. The protective member 5 is a flexible transparent film member, and thus, has strength enough to prevent damage once it is rolled, bent, or unrolled. The sealing member 6 is an annular elastic member that is interposed between the end part 21 of the container 2 and the top part 32 of the lid member 3 to enhance the adhesion. The inner diameter of the sealing member 6 is larger than the protruding part 31, and the outer diameter of the sealing member 6 is slightly larger than the inner diameter of the cylindrical skirt wall 34. Thus, when attached to the lid member 3, the sealing member 6 enters between the protruding part 31 and the cylindrical skirt wall 34 and is held between the top part 32 and the end part 21.

As shown in FIG. 2(A), when the device 1 is used, the annular member 4 is placed on the bottom surface of the container 2 that contains the liquid L and the fragile object S, and the liquid L and the fragile object S are put into or positioned in the space (first space) inside the annular member 4. Then, when the liquid level of the liquid L is lower than the height of the annular member 4, the liquid is further poured (liquid is added) so that the liquid level is adjusted to be equal to or slightly higher than the height of the annular member 4. Since the cross section of the annular member 4 is rectangular and there is no space in which gas is accumulated, the first space is filled with the liquid L. Then, the protective member 5 is placed so as to close the opening of the annular member 4, whereby the liquid surface of the liquid L contained in the first space is covered. Due to the film shape, the protective member 5 can cover the liquid surface without disturbing the liquid surface while gradually increasing the contact area with the liquid surface. Further, since the protective member 5 is transparent, the presence or absence of air bubbles can be visually confirmed, and the air bubbles can be easily removed by, for example, pushing the protective member 5 with a finger. As a result, a complete liquid-tight space surrounded by the bottom surface of the container 2, the annular member 4, and the protective member 5 can be formed.

Next, as shown in FIG. 2(B), the lid member 3 is attached to the container 2, and the protective member 5 is held (fixed) between the protruding part 31 and the annular member 4. This prevents the protective member 5 from displacing from the liquid surface. At this time, even if air bubbles enter between the protruding part 31 and the protective member 5, the air bubbles do not enter the first space because the protective member 5 is fluid impermeable. Further, the liquid L expelled by the protruding part 31 is held in the space G between the protruding part 31 and the container 2, and the sealing member 6 increases the hermeticity between the end part 21 of the container 2 and the top part 32 of the lid member 3. Thus, even if the liquid L contained in the space G is moved during transportation of the device 1, any problem such as leakage of the liquid L to the outside of the container 2 is unlikely to occur. Then, since the first space is completely liquid-tight and the liquid L is incompressible, the liquid L does not move even if the device 1 vibrates during transportation, so that an external force that deforms the fragile object S is not generated.

When the fragile object S is used, the lid member 3 is removed from the container 2 at the destination of transportation. In the device 1, the protruding part 31 does not enter the liquid-tight space (first space), and therefore, it is unlikely that a worker forcibly removes the lid member. Further, since the liquid surface in the liquid-tight space is protected by the protective member 5, it is unlikely that the fragile object S is damaged due to the wavy liquid surface when the lid member 3 is removed from the container 2. Since the film-shaped protective member 5 sticks to the liquid L by surface tension, it is unlikely that it sticks to the protruding part 31. The contact area between the protective member 5 and the liquid surface can be gradually decreased by pinching the protective member 5 at its end with tweezers or the like and rolling it up, whereby the surface waviness (surface waves) of the liquid can be minimized. Then, the fragile object S contained in the first space is taken out and used.

As described above, the device 1 according to the first embodiment can efficiently achieve a liquid-tight state with a simple mechanism and a simple operation, thereby providing great advantages in terms of operability and manufacturing cost. Further, the device 1 can bring the inside of the container into a complete liquid-tight state. Therefore, entry of air bubbles (gas) into the container can be prevented, and thus, the fragile object is not damaged due to the movement of air bubbles within the container caused by, for example, shaking of the container during transportation. Particularly when the fragile object is a laminate of sheet-shaped cell cultures, displacement or defect of the laminate due to the movement of air bubbles can be prevented. Therefore, the fragile object can be stored for a long time with the shape of the fragile object in the liquid being retained without being deformed.

Further, according to the device 1 of the first embodiment, the liquid-tight state can be easily released. Therefore, vibration of the container and the movement of the liquid caused by, for example, forced removal of the lid member by the worker can be minimized, and thus, damage of the fragile object can be prevented. In addition, since the device 1 allows the worker to do the work without contaminating the surroundings, the device 1 is suitable for use in a location where cleanliness is strictly controlled, such as a bio-clean room used for preparing a sheet-shaped cell culture and an intensive care unit where a sheet-shaped cell culture is used.

The device 1 has been described above on the basis of the first embodiment, but the present invention is not limited thereto, and may have various modifications. For example, the protective member 5 and/or the lid member 3 may be water repellent. That is, the portion where the protective member 5 and the lid member 3 contact, for example, the bottom surface of the protruding part 31 of the lid member 3, may be water repellent. This configuration can prevent the liquid L from sticking to the protective member 5 and the lid member 3, even when the liquid L enters between the protective member 5 and the lid member 3. Further, the protective member 5 may not be provided. That is, the device 1 is not configured such that the protruding part 31 of the lid member 3 enters the space (liquid-tight space) inside the annular member 4, whereby it is less likely that excessive force is applied during removal of the lid member 3. That is, the device 1 may be configured such that the protruding part 31 of the lid member 3 does not enter the space (liquid-tight space) inside the annular member 4, whereby it is less likely that excessive force is applied during removal of the lid member 3. Therefore, problems such as surface waviness of the liquid are less likely to occur even if the protective member 5 is not provided. Further, due to the bottom surface of the protruding part 31 being water repellent, the liquid surface is prevented from being pulled by the protruding part 31, which can suppress the surface waviness of the liquid.

Further, the sealing member 6 can also be variously modified. For example, the upper surface of the sealing member 6 may be fixed to the top part 32 of the lid member 3, and a circular groove may be provided in the lower surface. With this configuration, when the lid member 3 is attached to the container 2, the end part 21 of the container 2 is engaged with the circular groove, so that the airtightness of the second space is further increased, and the lid member 3 is less likely to be detached from the container 2. In addition, the sealing member 6 simultaneously pulls the lid member 3 downward, which increases the force to press the protruding part 31 of the lid member 3 against the annular member 4. Thus, the liquid-tightness of the first space is further enhanced. Furthermore, any addition or modification may be freely provided to the sealing member 6. For example, the sealing member 6 may be provided between the cylindrical skirt wall 34 of the lid member 3 and the outer peripheral surface of the container 2, or between the protruding part 31 of the lid member 3 and the inner peripheral surface of the container 2.

In addition, the annular member 4 can also be variously modified. For example, when the container is a commercially available petri dish, the inner peripheral surface of the petri dish is slightly inclined. Therefore, at least the outer peripheral surface of the annular member 4 may be tapered. With this configuration, the annular member 4 can be in close contact with the inner peripheral surface of the petri dish. In this case, a mark such as a marker or a small protrusion (raised dot) may be provided on the upper surface of the annular member 4 so that the upper and lower sides of the annular member 4 can be discriminated or distinguished. In a case where the protrusion is provided, the worker can discriminate or distinguish the upper side from the lower side only by touching the annular member 4 by his/her hand. However, when the protective member 5 is placed on the protrusion, the protective member 5 may rise. In view of this, a cutout may be formed in the protective member 5 at a position corresponding to the protrusion. This configuration can prevent the protective member 5 from rising.

Components used in the graft-transporting device may be substituted with other components which can function in the same or similar way or may be provided with other structure.

The graft-transporting device according to the disclosure here may be used according to following steps, for example.

(1) Prepare the container containing the fragile object and the liquid.
(2) Place the annular member on the bottom surface of the container.
(3) Place the protective member on the annular member.
(4) Attach the lid member to the container to form a liquid-tight state.
(5) Transport the device.
(6) Remove the lid member.
(7) Remove the protective member to release the liquid-tight state.
(8) Take out the fragile object for use.

Hereinafter, embodiments of gripping tools suitable for pressing and gripping the device 1 (container 2 and lid member 3) according to another aspect of the disclosure here will be described in detail with reference to the drawings.

Figure 4:
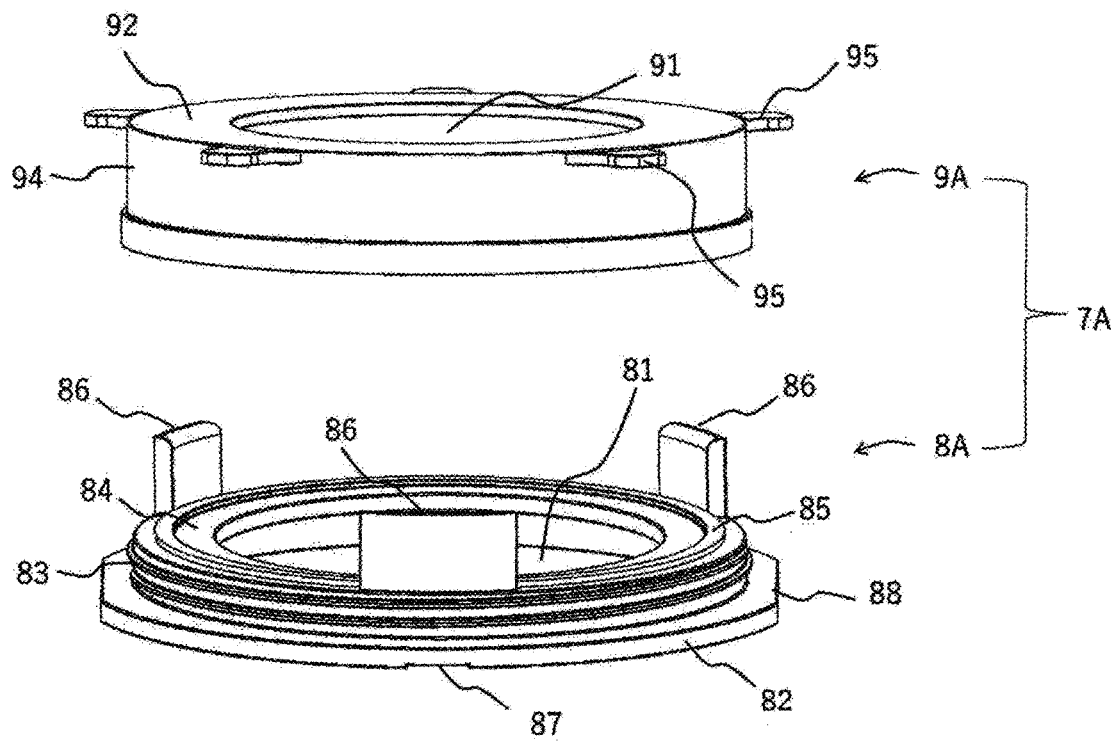
FIG. 4 is a perspective view of a gripping tool 7A according to a third embodiment.
Figure 5:
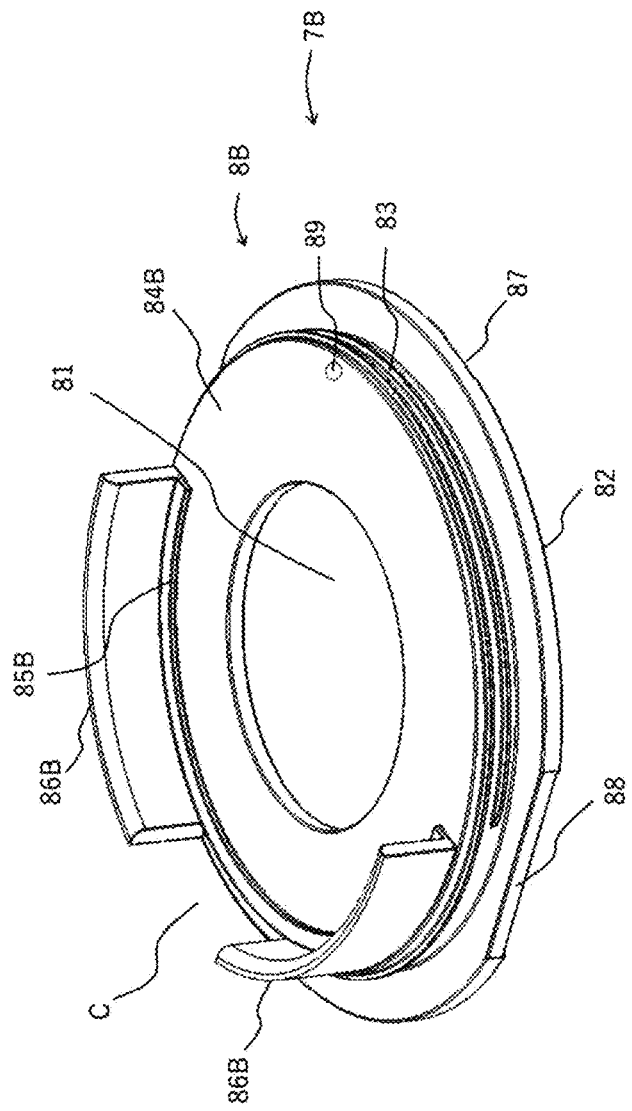
FIG. 5 is a perspective view of a gripping tool 7B according to a fourth embodiment.

FIG. 3 is a perspective view of a gripping tool 7 according to one embodiment of the disclosure, FIG. 4 is a perspective view of a gripping tool 7A according to another embodiment of the disclosure, and FIG. 5 is a perspective view of a gripping tool 7B according to a further embodiment of the disclosure. In the drawings of the present application, the dimensions of the various components are exaggerated, as appropriate, for facilitating the understanding of the description, and they may differ from the actual dimensions.

As shown in FIG. 3, the gripping tool 7 according to the present embodiment includes a base member 8 and a cover member 9. The gripping tool 7 can press and grip the device 1 including the container 2 (not shown) and the lid member 3 (not shown) for sealing the container 2 from above and below.

The base member 8 and the cover member 9 both have a circular shape, and can press the device 1, as appropriate, from above and below. The base member 8 includes an opening 81, a bottom part 82, a screw part (engagement part) 83, a placement part 84, and a ridge part 85. In the present embodiment, the engagement between the base member 8 and the cover member 9 is achieved by screwing. The placement part 84 has, on its upper surface, a placement surface on which the container 2 can be placed, and is provided with the opening 81 in the central portion. The placement part 84 has the annular ridge part 85 (elongated ridge) that surrounds the lower end of the container 2 when the container 2 is placed on the placement surface. Thus, the mounting position of the container 2 with respect to the base member 8 can be defined. The placement part 84 has a disk shape protruding upward from the bottom part 82, and the screw part 83 is provided on the side peripheral surface thereof. That is, the screw part 83 is located on the outer periphery of the base member 8 as shown in FIG. 3. The bottom part 82 has an outer diameter larger than that of the placement part 84, and serves as a bottom when the base member 8 is placed on a table or the like.

The cover member 9 includes an opening 91, a top part 92, a screw part (engagement part) 93, a cylindrical skirt wall 94, and a grip part 95. The top part 92 has a cover surface that can cover the upper surface of the lid member 3, and is provided with the opening 91 in the central portion. The top part 92 includes the cylindrical skirt wall 94 hanging or extending from the peripheral edge of the top part 92. The device 1 can be gripped by being surrounded by the top part 92, the cylindrical skirt wall 94, and the placement part 84. The screw part 93 is provided on the inner peripheral surface of the lower end of the cylindrical skirt wall 94. The cover member 9 can be screwed to the base member 8 by screwing (threadably engaging) the screw part 93 into the screw part 83 of the base member 8. Optionally, the inner diameter of at least a part (for example, the inner peripheral surface of the upper end of the cylindrical skirt wall 94) of the cylindrical skirt wall 94 may be set equal to the outer diameter of the lid member 3. With this configuration, the mounting position of the lid member 3 with respect to the gripping tool 7 can be defined.

When the gripping tool 7 is used, the lid member 3 is put on the container 2 containing an object S. At this time, a closed space (liquid-tight space) can also be formed by optionally putting the lid member 3 on the container 2 filled with the liquid L. Further, optionally, the sealing member 6 is provided between the container 2 and the lid member 3 to enhance the hermeticity, or the annular member is provided between the container 2 and the lid member 3 as described above to form a liquid-tight space. Next, the container 2 is placed on the base member 8. At this time, the container 2 can be positioned at the center of the placement part 84 using the ridge part 85. Further, the screw part 83 of the base member 8 is provided below the placement part 84, that is, the screw part 83 does not surround the side surface of the container 2. Therefore, when the container 2 is mounted/removed on/from the placement part 84, vibration can be suppressed by sliding the container 2 in the lateral direction. Next, the cover member 9 is attached to the base member 8. At this time, the lid member 3 can be positioned at the center of the cover member 9 (and the base member 8) using the cylindrical skirt wall 94.

In this way, the gripping tool 7 can define the relative position between the container 2 and the lid member 3 using the ridge part 85 of the base member 8 and the cylindrical skirt wall 94 of the cover member 9. When the device 1 is gripped using the gripping tool 7, the screw part 83 of the base member 8 and the screw part 93 of the cover member 9 are screwed together. During the screwing operation, the worker grips the grip part 95 provided on the outer peripheral surface of the cylindrical skirt wall 94 as a projecting part (or may be a groove). Thus, the container 2 and the lid member 3 can be tightened from above and below with a strong force. This is highly versatile, and is suitable for, for example, the case where the container 2 does not have a screw part, such as a general-purpose petri dish. Further, the lid member 3 can be configured not to rotate with respect to the container 2 (not to be screwed to the container 2). This configuration prevents the protective member 5 interposed between the container 2 and the lid member 3 from receiving a rotational force of the lid member 3, and thus is particularly advantageous. Further, particularly in a case where the elastic sealing member 6 or the annular member 4 is interposed, these members are accurately compressed between the container 2 and the lid member 3 which are accurately positioned relative to each other, whereby hermeticity is improved. Thus, this configuration is advantageous. The cover member 9 only needs to be screwed to the base member 8 by an amount corresponding to the height of the screw part 83. Therefore, the gripping operation is facilitated, and the gripping force can be easily adjusted. Thus, problems such as destruction of the device 1 can be prevented.

The base member 8 and the cover member 9 have the opening 81 and the opening 91, respectively, in the central portion. Therefore, the fixing position of the device 1 and the state of the liquid L, the object S, etc. contained in the device 1 can be constantly observed. This is particularly advantageous when the container 2 and the lid member 3 are made of a light-transmissive material. Even if a less visible object such as a sheet-shaped cell culture is used as the graft, light is emitted through one of the openings and the sheet-shaped cell culture can be viewed through the other opening. Thus, this configuration is advantageous. Further, in a case where the liquid-tight space is formed as described above, it is possible to press the lid member 3 against the container 2 while confirming that air bubbles, foreign matters, etc. do not enter the container 2 through the opening 91. Next, the device 1 is transported. Since the device 1 is firmly gripped by the gripping tool 7, problems such as detachment of the lid member 3 from the container 2 due to shaking during transportation can be prevented. Further, since the device 1 is surrounded by the gripping tool 7, it is protected from external impact. Finally, the gripping tool 7 is removed from the device 1 at the destination of transportation, and the device 1 is used there.

While the gripping tool has been described with reference to the illustrated embodiment, the invention is not limited thereto. For example, the screw parts 83 and 93 may be replaced with other engagement means having a function of pressing the device 1 from above and below, such as sliding engagement (for example, see Japanese Patent Application Publication No. 2006-315757 A), flange fitting (for example, see Japanese Patent Application Publication No. 2006-001582 A), and engagement using a ridge (for example, Japanese Patent Application Publication No. 2016-203985 A). The annular ridge part 85 can be replaced with other means capable of positioning the container 2 on the placement surface, such as a plurality of annularly arranged protrusions. For example, a fragile object (for example, a laminate of sheet-shaped cell cultures) can be contained as the object S. In that case, the fragile object can be transported with the shape thereof being retained by establishing a liquid-tight state in the container 2.

Next, another embodiment of the gripping tool will be described with reference to FIG. 4. The description below focusses primarily upon the differences between this embodiment and the earlier described embodiment. Features that are the same or similar to those described above are identified by the same reference numerals and a detailed description of such features is not repeated In FIG. 4, the dimensions of the various components are exaggerated, as appropriate, for facilitating the understanding of the description, and they may differ from the actual dimensions.

As shown in FIG. 4, a gripping tool 7A according to the present embodiment includes a base member 8A and a cover member 9A. In the present embodiment, the base member 8A further includes protruding walls 86, a groove 87, and a cutout part 88. The protruding walls 86 are plural upstanding walls that are positioned outside the ridge part 85 and that protrude from the placement part 84 beyond the height of the container 2. The groove 87 is formed in the lower surface of the bottom part 82 of the base member 8A so as to prevent the base member 8A from sticking to a working surface when the base member 8A is placed on a table or the like.

When the gripping tool 7A is used, the container 2 (not shown) is positioned at the center of the base member 8 using the ridge part 85. Next, the lid member 3 (not shown) is put on the container 2 along the protruding walls 86, whereby the lid member 3 can be positioned at the center of the base member 8. That is, the worker can define the relative position between the container 2 and the lid member 3 using the ridge part 85 and the protruding walls 86 of the base member 8A. This is particularly advantageous when the annular sealing member 6 and the annular member 4 are interposed between the container 2 and the lid member 3, because these members can be accurately pressed due to this configuration.

Next, the graft-transporting device 1 (not shown) is gripped. When gripping the device 1, the worker grips the grip part 95 provided as a projecting part projecting radially from the cover member 9A and the cutout part 88 formed in the side surface of the bottom part 82 of the base member 8A. Thus, the worker can easily perform the screwing operation. When the device 1 is used, the cover member 9A is unscrewed to remove the device 1 from the base member 8A. During the removal, the device 1 is exposed from gaps between the plurality of protruding walls 86, so that the device 1 is easily gripped. Further, since the plurality of protruding walls 86 is arranged so as to surround the container 2, the lid member 3 can be accurately positioned with respect to the container 2.

Next, fourth further embodiment of the gripping tool will be described with reference to FIG. 5. The description below focusses primarily upon the differences between this embodiment and the earlier described embodiment. Features that are the same or similar to those described above are identified by the same reference numerals and a detailed description of such features is not repeated. In FIG. 5, the dimensions of the various components are exaggerated, as appropriate, for facilitating the understanding of the description, and they may differ from the actual dimensions.

As shown in FIG. 5, a gripping tool 7B according to the present embodiment includes a cover member (not shown) and a base member 8B. The base member 8B includes a placement part 84B, a ridge part 85B, and a protruding wall 86B (the description of other components will not be repeated in view of the description above). The ridge part 85B is arranged on the placement part 84B in a semi-annular shape. The protruding wall 86B is arranged in a semi-annular shape on the outside of the ridge part 85B, and a cutout (gap) C is provided in a part of the protruding wall 86B (two or more circumferentially spaced apart protruding walls 86B may be provided in a semi-annular shape with a gap therebetween). That is, in the present embodiment, a half (the side reverse to the side where the ridge part 85B and the protruding wall 86B are provided) of the placement surface of the placement part 84B is flat and is not surrounded by a protruding wall(s) as shown in FIG. 5.

When the gripping tool 7B is used, the container 2 (not shown) is set such that the container 2 slides in the lateral direction (toward the ridge part 85B and the protruding wall 86B) from the side reverse to the side where the ridge part 85B and the protruding wall 86B are provided. At this time, the worker slides the container 2 on the flat surface of the placement part 84B, by which careless vibration of the container 2 can be suppressed. Next, the lid member 3 (not shown) is put on the container 2 while being pressed against the protruding wall 86B of the base member 8B, whereby the lid member 3 can be accurately positioned with respect to the container 2. When the device 1 (not shown) is used, the device 1 is removed from the base member 8A. When the device is removed, the side surface of the device 1 (the container 2 and/or the lid member 3) exposed from the cutout C is pressed, by which the device 1 slides on the flat surface. Thus, the device 1 can be removed. A protrusion 89 serving as a mark may be provided on the side facing the cutout C on the placement part 84B so that the sliding direction for sliding the device 1 on the base member 8A can be easily recognized. Accordingly, the device 1 can be accurately positioned on the placement part 84B simply by sliding the device 1 between the protrusion 89 and the cutout C. Further, the protrusion 89 may be provided on an extension of the ridge part 85B so as to face the cutout C so that the side surface of the device 1 abuts the protrusion 89. With this configuration, displacement of the device 1 can be prevented.

As described above, the gripping tools according to the various embodiments efficiently enable the container and the lid member to be in tight contact with each other with a simple mechanism and a simple operation, thereby providing great advantages in terms of operability and manufacturing cost. Further, the object contained in the container can be visually recognized from the outside, and thus, it is possible to easily confirm the state of the contained object, intrusion of foreign matters, and the like. Furthermore, the container and the lid member can be relatively positioned with high accuracy, whereby hermeticity is improved. In particular, when the elastic sealing member 6 and the annular member 4 are interposed between the container and the lid member, these members can be accurately pressed, so that the hermeticity is further improved.

Further, according to the gripping tool disclosed by way of example here, the container and the lid member can be reliably fixed in tight contact with each other, whereby problems such as detachment of the lid member from the container during transportation can be prevented. Particularly when the contained object is a laminate of sheet-shaped cell cultures, the object can be transported with the container being reliably brought into a liquid-tight state. Therefore, displacement or defect of the laminate due to air bubbles entering the container and moving in the container can be prevented. Accordingly, the object can be stored for a long time with its shape being retained without deformation.

The present invention is not limited to the abovementioned embodiments, and those skilled in the art could implement a gripping tool having different configurations and shapes by appropriately combining the configurations and shapes of the gripping tools according to the second to fourth embodiments. For example, the cover member 9 or the cover member 9A may be combined with the base member 8, the base member 8A, or the base member 8B, or the ridge part 85, the ridge part 85B, the protruding wall 86, or the protruding wall 86B may be combined with the base member 8, the base member 8A, or the base member 8B.

The detailed description above describes embodiments of a graft-transporting device and gripping tool representing examples of the inventive graft-transporting device and gripping tool disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims. In addition, components used in the present invention may be substituted with other components which can function in the same or similar way and/or have structural details added.

What is claimed is:

1. A graft-transporting device comprising:
a container having an interior in which is positioned liquid and a graft, the container includes a bottom surface and a side wall extending upwardly away from the bottom surface, the side wall possessing an inner surface so that the bottom surface and the inner surface of the side wall surround the interior of the container, the container also including an open end, the side wall of the container including an upper edge;
an annular member surrounding a centrally located first space, the annular member having oppositely facing first and second surfaces, the first surface of the annular member facing towards the bottom surface of the container and the second surface facing away from the bottom surface of the container, the annular member being positioned in the container so that the graft is located in the centrally located first space;

a lid positioned at and closing the open end of the container to seal the interior of the container;

a protective member overlying the first space of the annular member and positioned between the second surface of the annular member and the lid to protect the first space, the protective member being made of a fluid impermeable material so that gas and liquid do not pass through the protective member;

a second space in the interior of the container between the lid and the inner side wall surface of the container; and a seal positioned between and in contact with the upper edge of the side wall of the container and an inner surface of the lid.

2. The graft-transporting device according to claim 1, wherein the lid comprises a top part, a protruding part extending downward from the top part toward the bottom surface of the container, and a skirt wall extending downward from the top part toward the bottom surface of the container, the skirt wall being positioned radially outwardly of the protruding part so that the second space exists between the skirt wall and the protruding part.

3. The graft-transporting device according to claim 2, wherein the skirt wall of the lid possesses an inner surface and the side wall of the container possesses an outer surface, the skirt wall of the lid being positioned outside the side wall of the container so that the inner surface of the skirt wall of the lid faces the outer surface of the side wall of the container.

4. The graft-transporting device according to claim 2, wherein the protruding part of the lid possesses an outer surface and is positioned in the interior of the container so that the second space is defined between the outer surface of the protruding part and the inner surface of the side wall of the container.

5. The graft-transporting device according to claim 1, wherein the protective member is flexible.

6. The graft-transporting device according to claim 1, wherein the protective member and/or the lid is water repellent.

7. The graft-transporting device according to claim 1, wherein the lid comprises a top part, a protruding part extending downward from the top part toward the bottom surface of the container and terminating in a bottom surface, and a skirt wall extending downward from the top part toward the bottom surface of the container, the skirt wall being positioned radially outwardly of the protruding part so that the second space exists between the skirt wall and the protruding part, the bottom surface of the protruding wall being in contact with the protective member.

8. The graft-transporting device according to claim 1, wherein the graft is a sheet-shaped cell culture.

9. The graft-transporting device according to claim 8, wherein the sheet-shaped cell culture is a laminate.

10. A device to be detachably attached to a container that possesses an inside surface upstanding from a bottom surface and an open end opposite the bottom surface, and that contains a graft, the device comprising:

an annular member having a through hole passing through and opening to opposite surfaces of the annular member so that the through hole defines a first space surrounded by the annular member, the opposite surfaces of the annular member being first and second surfaces, the annular member having an outer periphery, the annular member being positionable in the container so that the first surface of the annular member faces the bottom surface of the container and the graft is located in the first space;

a lid positionable at the open end of the container to seal the container, the lid being positionable at the open end of the container after the annular member is positioned in the container so that the annular member is interposed between the lid and the bottom surface of the container;

the lid being configured so that when the lid is positioned at the open end of the container to seal the container, a second space exists between the lid and the inside surface of the container;

a protective member configured to be positioned on the second surface of the annular member so that the protective member is between the annular member and the lid to protect the first space, the protective member having an outer periphery, the protective member being configured so that when the protective member is positioned on the second surface of the annular member, the protective member completely covers the through hole in the annular member to protect the first space while the outer periphery of the protective member is located other than radially outwardly of the outer periphery of the annular member, the protective member being made of a fluid impermeable material so that gas and liquid do not pass through the protective member; and;

a sealing member configured to be interposed between an upper end of an upstanding wall of the container and an inner surface of the lid.

11. The device according to claim 10, wherein the protective member is flexible.

12. The device according to claim 10, wherein the protective member and/or the lid is water repellent.

13. The device according to claim 10, wherein the lid comprises a top part, a protruding part extending downward from the top part so that the protruding part extends toward the bottom surface of the container when the lid is positioned at the open end of the container to seal the container, and a skirt wall extending downward from the top part, the skirt wall being positioned radially outwardly of the protruding part so that the second space exists between the skirt wall and the protruding part.

14. A gripping tool comprising:
a cover member; and
a base member,
the gripping tool being configured to press and grip the device according to claim 10 from above and below.

15. A method comprising;
positioning an annular member in an interior of a container by introducing the annular member through an open end of the container, the container including a bottom surface positioned opposite the open end and an inside surface extending away for the bottom surface so that the interior of the container is surrounded by the bottom surface and the inside surface, the annular member being configured so that the annular member surrounds a first space and the annular member being located in the container so that a graft and liquid are in the first space, the annular member having oppositely facing first and second surfaces, the first surface of the annular member facing towards the bottom surface of the container and the second surface of the annular member facing away from the bottom surface of the container;

positioning a protective member on the second surface of the annular member so that the protective member overlies the first space and covers the through hole in the annular member to protect the first space, the protective member being made of a fluid impermeable material so that gas and liquid do not pass through the protective member;

positioning a lid on the open end of the container to seal the container while the annular member and the protective member are positioned in the interior of the container so that the annular member is interposed between the protective member and the bottom surface of the container while the protective member is interposed between the lid and the annular member, and a seal positioned between and in contact with an upper edge of a side wall of the container and an inner surface of the lid; and the lid being positioned on the open end of the container so that a second space exists between the lid and the inside surface of the container.

16. The method according to claim 15, wherein the liquid and the graft are positioned in the interior of the container before the positioning of the annular member in the interior of the container, and the second space being located above and radially outwardly of the first space.

17. A cell-culture transporting device comprising:

a container having an interior in which is positioned liquid and a sheet-shaped cell culture, the container including a bottom surface and a side wall extending upwardly away from the bottom surface, the side wall possessing an inner surface so that the bottom surface and the inner surface of the side wall surround the interior of the container, the container also including an open end;

an annular member positioned in the container, the annular member having a through hole passing through the annular member so that opposite open ends of the through hole open to respective opposite surfaces of the annular member, the opposite surfaces of the annular member including first and second surfaces, the first surface of the annular member facing towards the bottom surface of the container and the second surface of the annular member facing away from the bottom surface of the container, the sheet-shaped cell culture being positioned in the through hole in the annular member so that the sheet-shaped cell culture is located between the open ends of the through hole;

a protective member overlying the second surface of the annular member, the protective member being made of a fluid impermeable material so that gas and liquid do not pass through the protective member;

a lid positioned at and closing the open end of the container to seal the interior of the container;

a seal positioned between and in contact with an upper edge of the side wall of the container and an inner surface of the lid; and a second space in the interior of the container between the lid and the inner side wall surface of the container.

* * * * *